United States Patent [19]

Nomi et al.

[11] Patent Number: 5,529,820
[45] Date of Patent: Jun. 25, 1996

[54] FLEXIBLE, NON-POROUS TUBE AND A METHOD OF MAKING

[75] Inventors: Haruo Nomi, Sakuragaokanishi; Tetsuo Fujie, Corpo-Akoda; Masaki Yoshida, Okayama-ken; Akira Suzuki, Yamanashi-ken, all of Japan

[73] Assignees: Japan Gore-Tex, Inc.; Olympus Optical Corp., Ltd., both of Tokyo, Japan

[21] Appl. No.: 214,332

[22] Filed: Mar. 16, 1994

[30] Foreign Application Priority Data

Mar. 17, 1993 [JP] Japan .................................. 5-084017

[51] Int. Cl.$^6$ ..................................................... B32B 1/08
[52] U.S. Cl. ........................... 428/364; 428/365; 428/369; 600/139
[58] Field of Search ...................... 428/36.4, 36.5, 428/36.9

[56] References Cited

U.S. PATENT DOCUMENTS

| | | | |
|---|---|---|---|
| 3,734,139 | 5/1973 | Zafiroglu | 138/146 |
| 4,194,041 | 3/1980 | Gore et al. | 428/315 |
| 4,279,245 | 7/1991 | Takagi et al. | 128/4 |
| 4,304,010 | 12/1981 | Mano | 3/1.4 |
| 4,347,204 | 8/1982 | Takagi et al. | 264/127 |
| 4,443,511 | 4/1984 | Worden et al. | 428/252 |
| 4,613,544 | 9/1986 | Burleigh | 428/315.5 |
| 4,616,631 | 10/1986 | Takahashi | 128/6 |
| 4,619,641 | 10/1986 | Schanzer | 604/8 |
| 4,687,482 | 8/1987 | Hanson | 623/1 |
| 4,764,560 | 8/1988 | Mitchell | 524/506 |
| 4,816,339 | 3/1989 | Tu et al. | 428/421 |
| 4,882,113 | 11/1989 | Tu et al. | 264/127 |
| 4,925,710 | 5/1990 | Buck et al. | 428/34.5 |
| 4,945,125 | 7/1990 | Dillon et al. | 525/104 |
| 4,955,899 | 9/1990 | Della Corna et al. | 623/1 |
| 5,061,276 | 10/1991 | Tu et al. | 623/1 |
| 5,071,609 | 12/1991 | Tu et al. | 264/119 |
| 5,100,422 | 3/1992 | Berguer et al. | 606/151 |
| 5,104,400 | 4/1992 | Berguer et al. | 264/132 |

FOREIGN PATENT DOCUMENTS

| | | |
|---|---|---|
| 057590 | 8/1982 | European Pat. Off. . |
| 0256748 | 4/1987 | European Pat. Off. . |
| 0269449 | 11/1987 | European Pat. Off. . |
| 5536492 | 5/1976 | Japan . |
| 6140328 | 7/1984 | Japan . |
| 2126827 | 2/1989 | Japan . |
| 9117205 | 11/1991 | WIPO . |

OTHER PUBLICATIONS

Database WPI Week 7930, Derwent Publications Ltd., London, GB; AN 79- 55275B & JP-A-54-074 514 (Sumitomo Elec. Ind.) 14 Jun. 1979.

*Primary Examiner*—Mark D. Sweet
*Attorney, Agent, or Firm*—Wayne House

[57] ABSTRACT

A flexible, non-porous tube characterized by the fact that the void spaces present in the luminal surface of a substrate tube of porous polytetrafluoroethylene are filled with a silicone or fluorosilicone rubber, that a continuous coating of said silicone or fluorosilicone rubber is not present on the inner surface of said tube, and that the inner surface of said tube incorporates surfaces of both the polytetrafluoroethylene and the silicone or fluorosilicone rubber. The tube has excellent lubricity, resistance to contamination, resistance to chemicals, and has exceptional tube flexing properties. The flexible tube may be employed, for example, as a tube for removal of gas destructively tested by a gas sensor, as a tube for transporting various liquids, and particularly as a tube in medical applications, such as a forceps channel tube, an endoscope channel tube, a bodily fluid transport tube, catheter tube, or the like. A method of making the tube is also described.

8 Claims, 3 Drawing Sheets

FLEXIBLE, NON-POROUS TUBE AND A METHOD OF MAKING

FIELD OF THE INVENTION

The present invention relates to a flexible, non-porous tube and to a method for the manufacture thereof.

BACKGROUND OF THE INVENTION

There exists a need for a highly flexible, non-porous tubing for various, primarily medical applications. These applications typically involve the insertion of the tubing into a living body, either temporarily or as a permanent implant. Temporary applications include the use of the tubing as a catheter tubing to convey fluids into or out of a body, or alternatively as the tubing portion of a medical device such as an endoscope. Present endoscope channel tubes are made of porous expanded PTFE having a microstructure of nodes interconnected by fibrils, made as taught by U.S. Pat. Nos. 4,187,390 and 3,953,566. These tubes typically have a very small pore size with a fibril length of less than five microns. They are quite flexible, inert, biocompatible and lubricious. However, due to the porosity of the tubing, during use various contaminants such as proteins and calcium tend to penetrate the void spaces present on the inner surface of the tube and to adhere to the inner surface. The adhesion of contaminants to the inner surface of the tube resulted in a decline in the slip properties of the inner surface, and also impaired other tube functions such as its flexing properties. Moreover, washing and sterilization were necessary in order to remove the contaminants so that the tube could be reused. Washing and sterilization were time consuming, and represented a burdensome operation.

Various methods of improving this porous PTFE tube have been attempted. For example, a tube in which an elastomer coating has been formed on the inner surface of the tube has been proposed (Japanese Laid-Open Patent Applications 54-74514, 59-25725). However, while a tube furnished with such an inner surface elastomer coating has improved resistance to contamination, the continuous elastomer coating, which has slip properties inferior to those of PTFE, constitutes the inner surface of said tube, and as a result the slip properties of the inner surface are diminished. Moreover, large numbers of wrinkles are produced in the coating during flexing, resulting in a further loss of slip properties.

In Japanese Patent Publication 61-47547, a porous PTFE tube wherein portions of said tube were impregnated with a solution of a vinylidene fluoride/tetrafluoroethylene copolymer, polyvinyl chloride, or another synthetic resin lacking elastic force, and then heated and dried so that portions of the tube were filled with the synthetic resin and rendered rigid thereby is disclosed. The mechanical strength of the tube was increased by rendering portions of it rigid, but the overall flexibility of the tube was significantly diminished; moreover, since the resin was contained in only a portion of the inner surface of the tube, the resistance of the inner surface to contamination was not improved.

In Japanese Laid-Open Patent Application 2-147065, a tube for medical use wherein the surface of a porous resin tube was coated with a solution of a synthetic resin such as polyvinyl chloride, dried, and a water soluble polymer coating formed on the resin surface was proposed. However, since this tube contained a synthetic resin which possessed no elastic force, the overall flexibility of the tube was insufficient; moreover, the synthetic resin was merely applied to the tube surface in the form of a solution and then dried so that formation of a continuous thin coat of said resin was unavoidable, with the result that the slip properties of the surface were diminished.

A porous resin tube which contained a synthetic resin was also disclosed in Japanese Laid-Open Patent Application 55-82884. However, in the case of this tube as well, the synthetic resin was applied to the tube inner surface in the form of a solution, caused to impregnate the pores, and cured, with the result that a continuous coat of the synthetic resin necessarily formed on the inner surface, thus diminishing the slip properties of the inner surface. Moreover, since the resin contained in the tube was a thermoplastic resin, it lacked a crosslinked structure, and thus the resistance to chemicals was poor.

SUMMARY OF THE INVENTION

The present invention is intended to offer a flexible, non-porous tube which has excellent tube flexing properties and whose inner surface has excellent slip properties, resistance to contamination, and resistance to chemicals, and a method for the manufacture thereof.

The present invention offers a flexible, non-porous tube, which is characterized by the fact that the void spaces present in a substrate tube consisting of polytetrafluoroethylene having a fine porous structure are filled with a silicone rubber, that a continuous coat of said silicone rubber is not present on the inner surface of said tube, and that the inner surface of said tube comprises both said polytetrafluoroethylene and said silicone rubber. The silicone rubber may be a fluorosilicone rubber.

The present invention further offers a flexible, non-porous tube, wherein the inner surface comprises PTFE and silicone rubber and wherein the outer surface of the tube comprises porous PTFE wherein the void spaces of the porous PTFE are not filled with a solid material.

The present invention also offers a method for manufacturing a flexible tube having excellent inner surface slip properties, resistance to contamination, and resistance to chemicals, wherein said method for manufacturing a flexible tube is characterized by the fact that (i) a flexible tube consisting of a polytetrafluoroethylene having a fine porous structure is provided as the substrate tube; (ii) the inner surface of said tube is brought into contact with an organic solvent solution of a curing silicone rubber precursor composition or an organic solvent solution of a curing fluorosilicone rubber precursor composition, and said solution caused to impregnate the void spaces of said substrate tube; (iii) a curing reaction of the curing rubber precursor composition that fills the void spaces of said substrate tube is brought about, so that a rubber having a crosslinked structure is formed, and (iv) the continuous rubber coat of a crosslinked structure formed on the inner surface of the substrate tube filled with the crosslinked rubber is removed, so that surfaces of both polytetrafluoroethylene and crosslinked rubber are exposed at the inner surface.

DETAILED DESCRIPTION OF THE INVENTION

Figure 1:
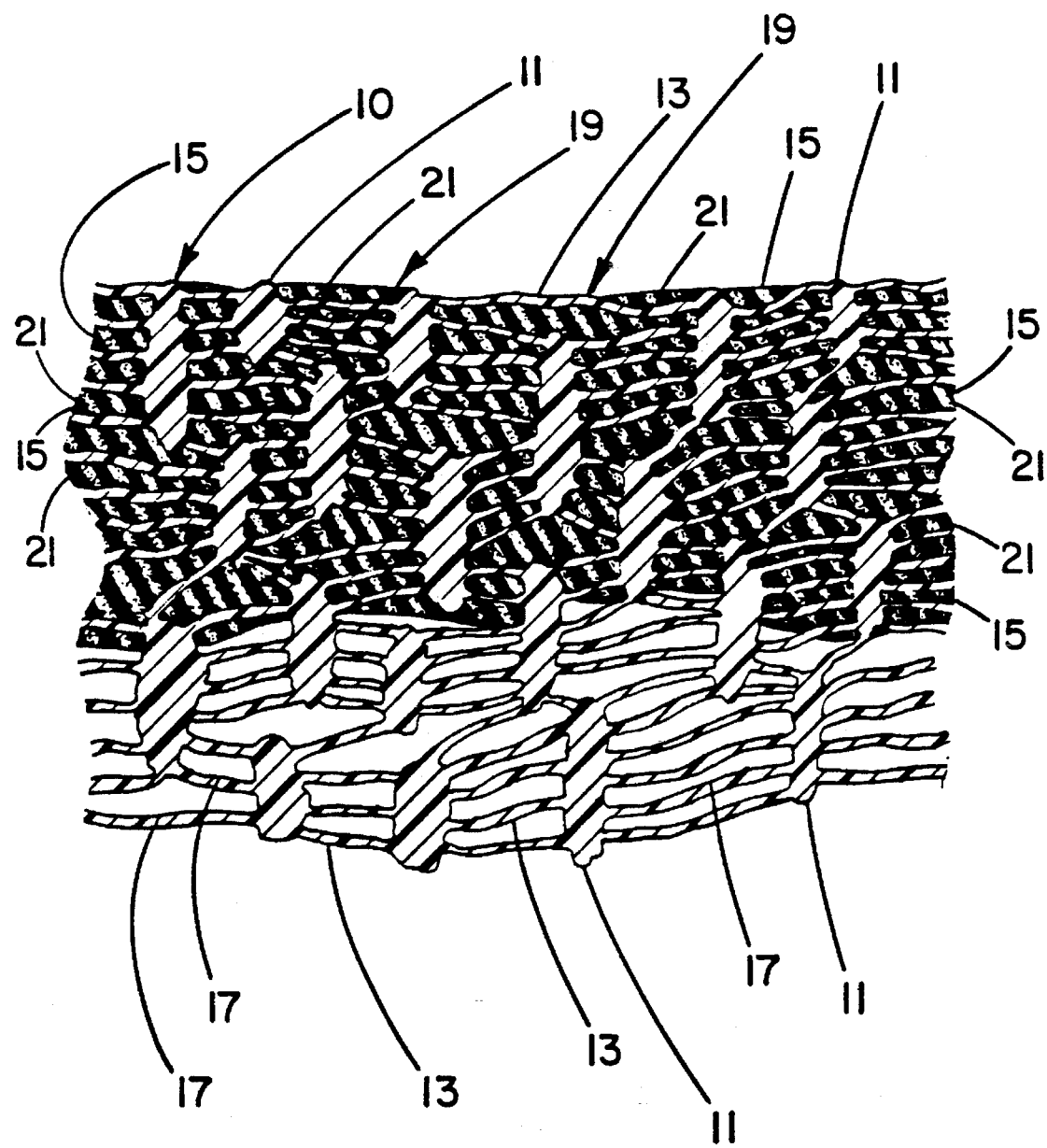
FIG. 1 is a magnified cross sectional schematic view describing the tube of the present invention.

The tube of PTFE having a fine porous structure which is employed as the substrate tube in the present invention is of a conventional known type, and may be manufactured, for example, by the following methods.

(1) A method wherein mixture of a PTFE resin having crystallinity of about 95% or above and a liquid lubricant (solvent naphtha, white oil, or the like) is extruded into a tube shape from an extrusion unit, and after either removing the liquid lubricant or leaving it, the resulting tube is subjected, in an unsintered state at 327° C. or below, to uniaxial or biaxial stretching at a rate of, for example, 10% per second, and if desired, heat treated at a temperature at or above the melting point of the PTFE. Tubes of this type are made as taught by U.S. Pat. Nos. 4,187,390 and 3,953,566.

(2) A method wherein a flat film is manufactured following the procedure of the above method (1), with the exception that the molded article extruded from the extrusion unit takes the form of a flat film, the flat film is wrapped around the outer surface of a core material (such as a pipe, wire material, or rod formed form metal, plastic, or the like), and baked at a temperature at or above the melting point of the PTFE, preferably 345° C. or above, and more preferably 350° to 375° C. In this latter method, the manner in which the flat film is wrapped around the core material, such as in a cigarette-roll having a longitudinally-oriented seam or spiral roll having a helically oriented seam, may be freely selected. The number of wrapping turns in the cigarette roll configuration is ordinarily about 1 to 5; in the spiral configuration, it is ordinarily about 1 to 5 layers.

The PTFE tube obtained in the manner described above has a fine porous structure in which many nodes are interconnected by fibrils. The properties of the fine porous structure of the PTFE which constitutes the tube may be described in common terms as follows: a fibril length of 0.05 to 30 microns, and preferably 0.2 to 10 microns, and a void volume of 20 to 70%, and preferably 30 to 50%. The inside diameter of the tube may differ depending upon its intended use, but is ordinarily about 1 to 20 mm, while the tube wall thickness is 20 to 2000 microns, and preferably 100 to 600 microns.

The fibril length of porous expanded PTFE that has been expanded in a single direction is defined herein as the average of ten measurements between nodes connected by fibrils in the direction of expansion. Ten measurements are made in the following manner. First, a photomicrograph is made of a representative portion of the sample surface, of adequate magnification to show at least five sequential fibrils within the length of the photomicrograph. Two parallel lines are drawn across the length of the photomicrograph so as to divide the photograph into three equal areas, with the lines being drawn in the direction of expansion and parallel to the direction of orientation of the fibrils. Measuring from left to right, five measurements of fibril length are made along the top line in the photograph beginning with the first node to intersect the line near the left edge of the photograph and continuing with consecutive nodes intersecting the line. Five more measurements are made along the other line from right to left beginning with the first node to intersect the line on the right hand side of the photograph. The ten measurements obtained by this method are averaged to obtain the fibril length of the material.

The method for obtaining the flexible tube which pertains to the present invention using the above-mentioned fine porous PTFE tube as the substrate tube is as follows. First, the inner surface of the substrate tube is brought into contact with a solution prepared by dissolving a curing silicone rubber precursor composition or a curing fluorosilicone rubber precursor composition in an organic solvent, and using the solution to impregnate the void spaces of the tube wall at the inner surface of the tube.

The resulting tube is shown in the magnified schematic view of FIG. 1 that represents a longitudinal cross section of the tube wall. The microstructure of the porous expanded PTFE tube 10 comprises a series of nodes 11 interconnected by fibrils 13 and having void spaces 15 and 17 between fibrils 13. At the luminal surface 19 of the tube 10, the void spaces 15 are filled with a silicone or fluorosilicone rubber 21, whereby the luminal surface 19 of the tube 10 comprises both the PTFE material of the nodes 11 and fibrils 13 at the tube luminal surface 19 as well as the silicone or fluorosilicone rubber 21 that fills the void spaces 15 of the porous expanded PTFE at the luminal surface 19. Other void spaces 17 away from the luminal surface 19 remain unfilled by the silicone or fluorosilicone rubber.

The curing silicone rubber precursor composition referred to in this specification contains a silicone rubber precursor and a curing catalyst, the curing reaction of which produces a silicone rubber having a crosslinked structure. Silicone rubber precursor refers to the starting material components for the curing reaction, and includes siloxane or polysiloxane having reactive groups, alkoxysilane or a partially hydrolyzed form thereof, and copolymeric siloxane having reactive groups. Known curing silicone rubber precursor compositions include normal temperature-curing types, low temperature-curing types, and high temperature-curing types; the use of low temperature-curing types and high temperature-curing types is preferable in the present invention.

Room temperature-curing and high temperature-curing compositions include two-pack types. These two-pack types deliver a silicone rubber having a crosslinked structure by means of a reaction between siloxanes having reactive groups such as SiOH, SiOR (where R is an alkyl group), SiH, SiCH=$CH_2$, or the like in the presence of a catalyst. The two-pack compositions are divided into condensation reaction types and addition reaction types. The condensation reaction types include those employing a dehydration condensation reaction between silanols, a dealcoholation condensation reaction between silanol and alkoxy siloxane, or a dehydrogenation condensation reaction between SiH and silanol. The addition reaction types include those employing addition reaction between vinyl groups, allyl groups, or other unsaturated groups and SiH. A suitable curing catalyst is selected depending upon the type of curing reaction. For example, metal organic acid salts, organic amines, quaternary ammonium salts, and the like are employed in reactions of condensation reaction types. Palladium or platinum black, platinum asbestos, chloroplatinic acid, or other form of platinum are employed in reactions of addition reaction types. The above-mentioned composition may also contain common assistant components, such as fillers, silicone oil, and the like. A description of silicone rubbers is provided in, for example, "Purasuchikku Zairyo Koza (9), Keiso Jushi" (A Course in Plastic Materials (9), Silicone Resins), Nikkan Kogyo Sha, pp. 118–123.

In the present invention, the above-mentioned curing silicone precursor composition is used in the form of an organic solvent solution. Examples of organic solvents used for this purpose include methyl ethyl ketone, toluene, xylene, and the like. The concentration of the silicone precursor within the solution should be such that a viscosity allowing for ease in impregnation of the void spaces in the tube wall by the solution (0.5 to 15 c.p. at 25° C.) is achieved; ordinarily, this concentration is 10 to 50 wt %, and preferably 20 to 40 wt %.

The curing fluorosilicone precursor composition referred to herein contains a fluorosilicone precursor and a curing catalyst, the curing reaction of which produces a fluorosilicone rubber having a crosslinked structure. Fluorosilicone rubber precursor refers to the starting material components for the curing reaction, and includes fluorosiloxane or polyfluorosiloxane having reactive groups, fluoroalkoxysilane or a hydrolyzed form thereof, and copolymeric fluorosiloxane having reactive groups. In the present invention, it is particularly desirable to use a copolymer of a siloxane having fluoroalkyl groups (such as a trifluoropropyl siloxane cyclic trimer), an alkyl siloxane (such as a dimethyl siloxane cyclic trimer), and a siloxane having reactive groups. The fluorosiloxane referred to herein is a siloxane containing fluoroalkyl groups. Curing fluorosilicone precursor compositions include normal temperature-curing types, low temperature-curing types, and high temperature-curing types; the use of low temperature-curing types and high temperature-curing types is preferable in the present invention.

Room temperature-curing and high temperature-curing compositions include two-pack types. These two-pack types deliver a fluorosilicone rubber having a crosslinked structure by means of a reaction between siloxanes having reaction groups such as SiOH, SiOR (where R is an alkyl group), SiH, SiCH=CH2, or the like in the presence of a catalyst. The two-pack compositions are divided into condensation reaction types and addition reaction types. The condensation reaction types include those employing a dehydration condensation reaction between silanols, a dealcoholation condensation reaction between silanol and alkoxy siloxane, or a dehydrogenation condensation reaction between SiH and silanol. The addition reaction types include those employing addition reaction between vinyl groups, allyl groups, or other unsaturated groups and SiH. A suitable curing catalyst is selected depending upon the type of curing reaction. For example, metal organic acid salts, organic amines, quaternary ammonium salts, and the like are employed in reactions of condensation reaction types. Palladium or platinum black, platinum asbestos, chloroplatinic acid, or other form of platinum are employed in reactions of addition reaction types. The above-mentioned composition may also contain common assistant components, such as fillers, silicone oil, and the like.

In the present invention, the above-mentioned curing fluorosilicone precursor composition is used in the form of an organic solvent solution. Examples of organic solvents used for this purpose include methyl ethyl ketone, toluene, xylene, and the like. The concentration of the fluorosilicone precursor within the solution should be such that a viscosity allowing for ease in impregnation of the void spaces in the tube wall by the solution (0.5 to 15 c.p. at 25° C.) is achieved; ordinarily, this concentration is 10 to 50 wt %, and preferably 20 to 40 wt %.

Any of several methods may be used for impregnating the void spaces of the tube wall with the above-mentioned curing silicone precursor composition solution or curing fluorosilicone precursor composition solution (hereinafter termed "solution") as long as the solution is brought into contact with the inner wall of the tube. For example, a method wherein the solution is coated onto the inner wall of the tube, a method wherein the solution is introduced into the space inside the tube, and the solution-containing tube then slowly rotated while maintaining it in the horizontal direction, or a method wherein the tip of the tube is inserted into the solution, the pressure at the other end of the tube reduced, and the solution sucked into the tube walls may be employed.

The solution with which the void spaces in the tube wall is impregnated in accordance with the present invention has a low viscosity, as noted above, and it is therefore possible for the void spaces in the tube wall to become smoothly impregnated with the solution merely by bringing the solution into contact with the tube wall.

The porous tube whose tube wall void spaces have been impregnated with the solution in the process described above is subjected to normal temperature or heat to evaporate the organic solvent as well as to bring about a curing reaction of the silicone rubber precursor composition or fluorosilicone rubber precursor composition (hereinafter termed "composition") present in the void spaces inside the tube to produce a silicone or fluorosilicone rubber (hereinafter termed "rubber") having a crosslinked structure, so that the void spaces are filled with rubber having a crosslinked structure. The curing reaction of the composition within the void spaces may be brought about simultaneous with or subsequent to evaporation of the organic solvent. The specific curing reaction is that most suitable for the type of composition. For example, in the case of a normal temperature-curing composition, curing may be brought about while evaporating the organic solvent at normal temperature or under heating. Heat-setting compositions may be cured by first evaporating the organic solvent at a temperature below that at which the composition curing reaction occurs, and then heating the composition to the temperature at which the composition curing reaction occurs to bring about curing. If the void spaces of the tube do not become filled with sufficient crosslinked rubber in the course of the above series of operations, the above series of operations may be repeated.

The porous tube whose tube wall void spaces have been filled with rubber having a crosslinked structure by the process described above also has a coat of the same crosslinked rubber which has formed on its inner surface. In the present invention, this rubber coat is removed. In order to accomplish this, the inner surface of the tube should be rubbed with an inserted jig. The jig may be a metal or ceramic rod, sphere, column, cone or other rigid body having a smooth surface, a plastic nylon brush, or the like. By rubbing this jig against the inner surface of the tube about two to five times, the rubber film on the inside tube surface may be peeled away so that the surfaces of both the PTFE (PTFE nodes and fibrils) which constitutes the tube and the rubber which fills the void spaces of the tube are exposed, so that an inner surface comprising both the PTFE surface and the rubber surface is formed. The resulting inner surface is characterized by the fact that no continuous rubber surface coating is present on the inner surface, that the PTFE surface and the rubber surface form a tight, non-porous surface, and that the rubber takes the form of a silicone rubber or fluorosilicone rubber having a crosslinked structure, with the result that the tube which pertains to the present invention has excellent flexing properties (flexibility), the inner surface has excellent slip properties, resistance to contamination, and resistance to chemicals, and has exceptional heat resistance and durability.

Alternative methods for removing the continuous rubber coat, apart from the aforementioned jig method, include spraying the tube inner surface with a high pressure stream, for example, a high pressure air or high pressure water stream. These methods may be used in combination with above-mentioned methods.

The flexible tube which pertains to the present invention may also take the form of a multilayer structure comprising two or more layers by means of laminate bonding various types of layers to the outer surface of the tube as necessary. For example, the tube may be furnished with a second layer consisting of a gas tight material and a third layer consisting of porous PTFE placed thereupon to yield a flexible tube having a three layer structure.

An example of the manufacture this type of flexible tube having a three-layer structure is to form a second layer consisting of a gas tight material on the outer surface of a substrate tube whose tube wall has not been filled with rubber. Gas tight materials which may be used for this purpose include synthetic resin films, metal foils furnished with synthetic resin layers, or other conventional materials. FEP (tetrafluoroethylene/hexafluoropropylene copolymer), PFA (tetrafluoroethylene/perfluoroalkylvinyl ether copolymer), polytetrafluoroethylene, or other fluororesin, fluororubber, polyurethane, polyimide, nylon, polyester, polyvinyl chloride, polyethylene, or other polyolefin may be employed as the synthetic resin.

Examples of metal foils include aluminum foil, copper foil, and titanium foil. Metal foils furnished with synthetic resin layers may be obtained by laminate bonding films consisting of the above-mentioned synthetic resins to at least one surface of the metal foil, or by applying a solution of the above-mentioned synthetic resin or a common adhesive solution thereto, and drying it.

Methods for forming a gas tight material layer on the outer surface of the substrate tube include a method wherein a gas tight material of film form is wound onto the outer surface of the substrate tube, with or without an adhesive, a method wherein a synthetic resin solution is applied and dried, a method wherein a curing resin is applied and cured, or a method wherein a the substrate tube is covered with a heat shrinking synthetic resin tube, which is then heat shrunk. The thickness of the gas tight layer should be 10 to 200 microns, and preferably 20 to 100 microns.

The gas tight material second layer formed in the manner described above may in turn be wound with a third layer consisting of a PTFE film having a porous structure as the material. The material described above may be employed as this PTFE film having a porous structure, and the cigarette roll or spiral roll method noted above may be used as the rolling technique for said film. The thickness of the third layer should be 50 to 500 microns, and preferably 100 to 200 microns.

A tube comprising the above-mentioned second and third layers formed on the substrate tube is heated to a temperature at which the synthetic resin which constitutes the gas tight material of the second layer melts, ordinarily 200° to 400° C. and preferably 330° to 390° C. The heating operation yields a multilayer tube which is entirely fused into a single unit. When forming the second and third layers on the substrate tube, each layer may also be caused to adhere to each other by using an adhesive.

The void spaces of the inner surface of the porous PTFE (first layer) of the multilayer tube formed in the above manner are then filled with a crosslinked rubber and the rubber coat formed on the inner surface removed, following the procedures described above.

When manufacturing a multilayer tube in accordance with the present invention, it is also possible to use, in place of the above-mentioned tube whose wall has not been filled with rubber, a single-layer flexible tube which pertains to the present invention that has been formed by filling its void spaces with rubber and removing the rubber coat that has adhered to the inner surface beforehand as the substrate tube which constitutes the first layer. In this case, the process of filling the void spaces of the tube wall with rubber may be omitted during manufacture of the above-mentioned multilayer tube.

When using a rubber pre-filled tube as the substrate tube, the continuous rubber coat may alternatively be removed subsequent to forming the multilayer structure.

The single-layer flexible tube which pertains to the present invention, whose tube wall void spaces have been filled with rubber, may be made into a flexible tube having a two-layer structure by forming a second layer on its outer surface. In this case, a PTFE film of solid, non-porous structure may be used as the material for the second layer. This type of two-layer structure tube possesses inner and outer surfaces which are smooth and which have good slip properties, and which moreover have exceptional resistance to contamination, resistance to microorganisms, and resistance to adhesion by organic matter. The solid, non-porous PTFE film employed here may be formed by extrusion of a mixture of PTFE resin having about 95% crystallinity or above and a liquid lubricant (such as solvent naphtha or white oil) from an extruder to yield a film. After either removing the liquid lubricant or leaving it, the extrusion molded film is subjected, in an unsintered state at 327° C. or below, to uniaxial or biaxial stretching at a rate of 10% per second to yield a porous PTFE film to which pressure is then applied to yield a solid film. Methods for solidifying the porous PTFE film include, for example, a method wherein the porous PTFE film is placed between synthetic resin sheets, such as polyester films, and passed through pressure rollers, or a method wherein the porous PTFE film is placed between sheets of metal foil, such as aluminum foil, heated to a temperature at or above the melting point of the PTFE, and passed through pressure rollers. In the former method, the temperature may be selected from a range extending from normal temperature to a temperature below the melting point of the synthetic resin. The applied pressure will vary depending upon the flexibility of the rollers and other factors, but is ordinarily 50 kg/cm$^2$ or above, and preferably 100 to 250 kg/cm$^2$. In the latter method, solidification may be accomplished at a lower pressure than in the former method. In either method, the porous PTFE film should be solidified by compression to 80% or less, and preferably 20 to 60% of its thickness prior to compression. An alternative method for solidifying the porous PTFE film is a method wherein the porous film is wound one or more turns around the outside surface of a pipe, the wound assembly is inserted into one side of another pipe, ring, or die furnished with a passage having a diameter smaller than the outside diameter of the wound assembly but somewhat larger than the outer diameter of the pipe and vigorously pulled out from the other side. In this method the wound assembly will be strongly compressed inwards from its outer surface as it passes through the passage, and the porous film of said wound assembly will be compressed into a solid film by the compressive force. The diameter of the passage should be such that the thickness of the film formed on the outer surface of the wound assembly pipe is compressed to 80% or less, and preferably 20 to 60% of its thickness prior to compression.

The solid film formed from the porous PTFE film in the manner described above has a Gurley number (time required for 100 cm³ air to flow through a surface area of 6.45 cm² at a water column pressure of 12.4 cm) of 500,000 seconds or greater, and the film is thus essentially completely gas tight. When manufacturing a solid film by applying pressure to a porous PTFE film, it is preferable to use a biaxially drawn film rather than a uniaxially drawn film as the porous PTFE film, since it is easier to obtain a uniform thin film from a biaxially drawn porous PTFE film, and since the resulting film is more flexible. The solid film should be as thin as possible, ordinarily 50 microns or less, and preferably within the range of 5 to 30 microns.

In the two-layer flexible tube described above, filling the wall of the tube whose first layer consists of porous PTFE with rubber may be accomplished by filling the substrate tube with rubber prior to assembly of the two-layer tube, as was done with the multilayer flexible tube described above, or by filling it with rubber after assembling the two-layer tube.

Figure 2:
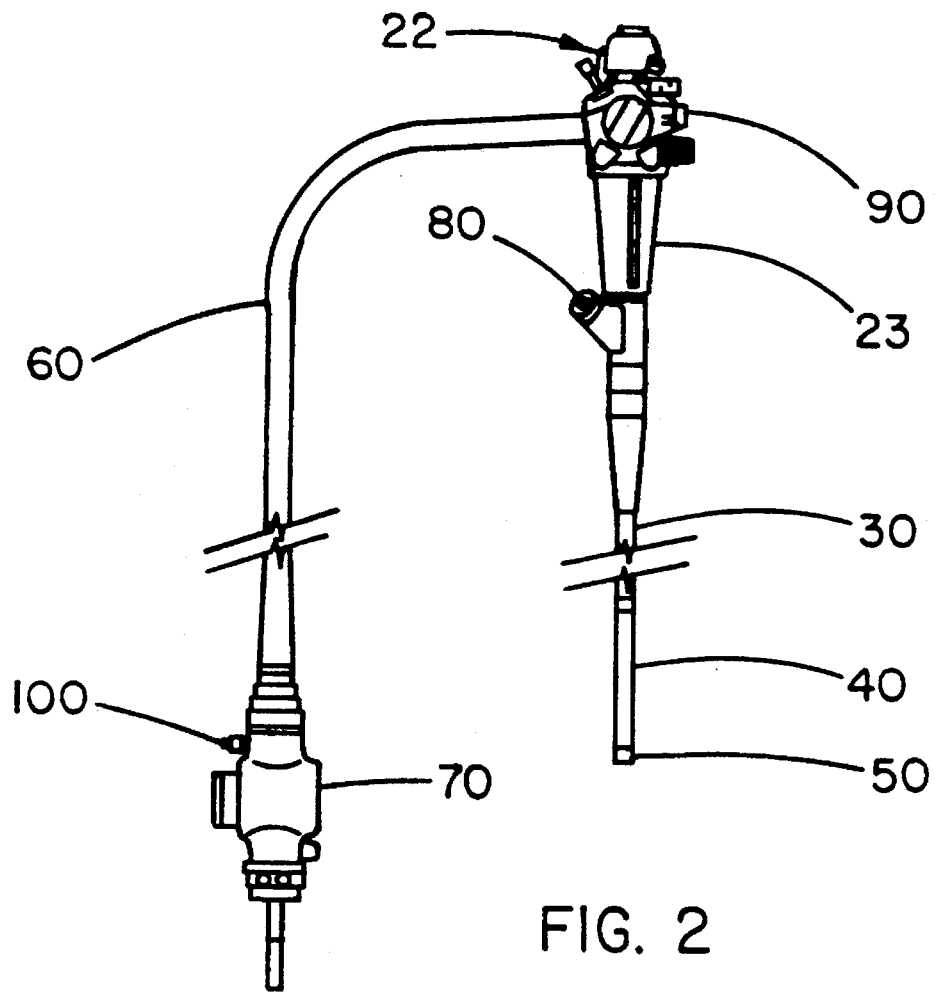
FIG. 2 is a schematic explanatory diagram of an electronic endoscopic unit.

As shown in FIG. 2, an electronic endoscopic unit 22 comprises an operating section 23, an insertion section 30, a bending section 40, a tip component 50, a universal cord 60, and connector 70. While not shown in the figure, an endoscopic image control unit, a monitor, a light source, and a suction device are also used. The operating section 23 is furnished with an instrument insertion port 80 and a suction switching control mechanism 90. Connector 70 is furnished with a suction tube attachment nozzle 100 for connection to an external suction unit.

Figure 3:
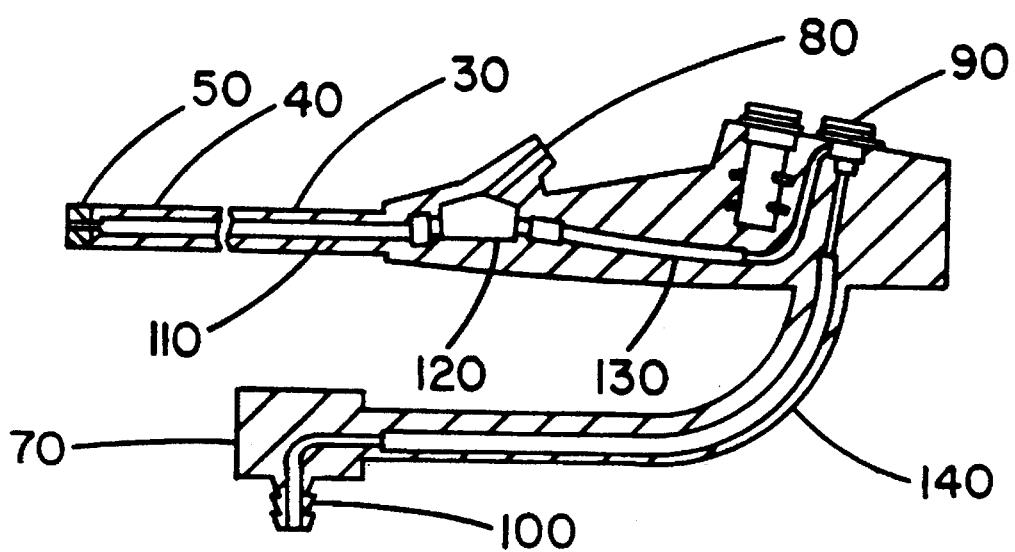
FIG. 3 is a schematic explanatory diagram of the structure of the suction and instrument insertion conduits in an electronic endoscopic unit.

FIG. 3 illustrates the structure of the suction and instrument insertion conduits within the electronic endoscopic unit. As may be seen in the figure, one end of the first suction tube 110 which is housed in the insertion section 30 and the bending section 40 is attached to the tip component 50 through a pipe; a detailed illustration of this connection is presented in FIG. 4. The other end of the first suction tube 110 is connected to the first port of a branch component 120 which is furnished with three ports in communication and which is housed in the operating section 20; a detailed illustration of this connection is presented in FIG. 5. The second port of the branch component 120 is connected to the instrument insertion port 80. The third port of the branch component 120 is connected to the first port of the suction switching control mechanism 90 through a second suction tube 130. The second port of the suction switching control mechanism 90 is connected to the suction tube attachment nozzle 100 through a third suction tube 140. The tube which pertains to the present invention may be used as the first suction tube 110, of which the greatest degree of flexing resistance to vigorous bending is required, and if necessary, may also be used as the second suction tube 130 and/or the third suction tube 140.

Figure 4:
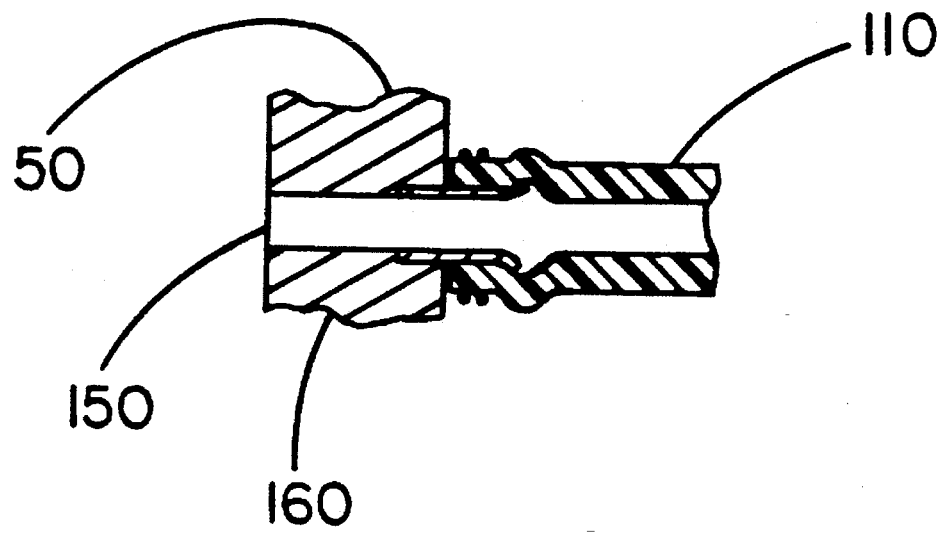
FIG. 4 is a diagram of an example of the structure of a conduit connection section of the endoscopic unit.

FIG. 4 shows the section in which the first suction tube 110 and the tip component 50 are fastened. The tip component 50 is furnished with a through-hole 150, into one end of which a pipe 160 is attached or soldered to fasten it. The first suction tube 110 is attached and fastened to the other end of pipe 160. In order to prevent the tube from coming off or the instrument inserted into the tube from catching on the pipe edge, one end of the pipe 160 widens into a taper. When a soft tube and a rigid pipe are connected in this manner, extreme flexing of the connection section occurs when the bending section of the endoscope is bent. In order to prevent this, the end of the first suction tube 110 is subjected to a rigidification process and furnished thereby with a section having moderate rigidity so that a smooth bending mode is achieved. Examples of rigidification processes include, for example, heating the end of the tube to solidify the porous structure of the PTFE, or impregnating the end with a resin to solidify the porous structure of the PTFE. It is also possible, using a surface treatment solution consisting of metallic sodium dispersed in naphthalene, to liberate the fluorines on the surface of the first layer of the tube by means of a chemical reaction, thus rendering the layer polarized, or to perform surface roughening by irradiation with plasma, in order to increase the bonding strength of the pipe 160 and the first suction tube 110. The bonding strength of the pipe 160 and the first suction tube 110 may be further improved by winding a gut thread over the fitted pipe 160 and first suction tube 110 and covering the gut thread with an adhesive.

Figure 5:
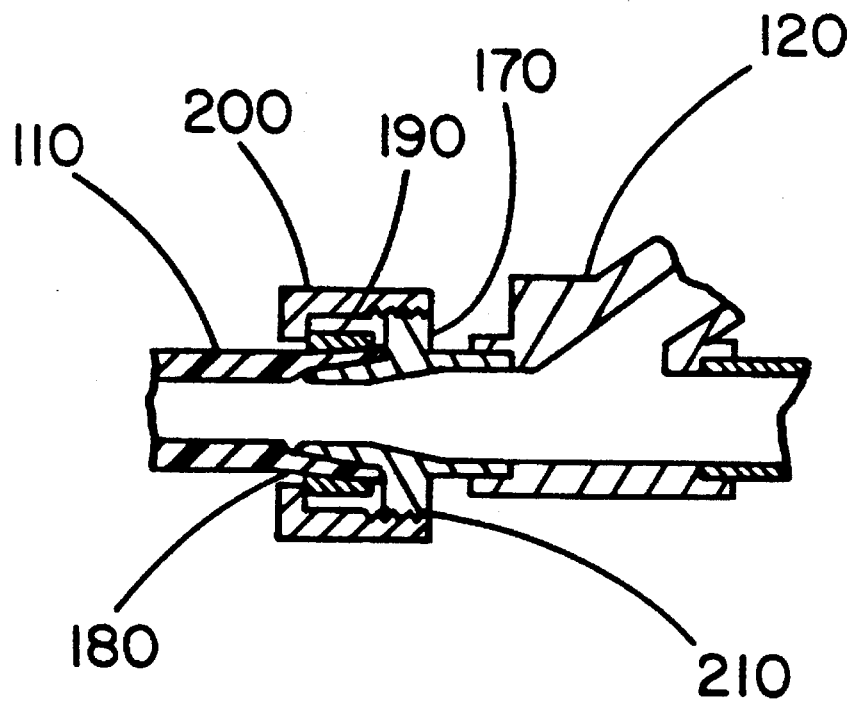
FIG. 5 is a diagram of another example of the structure of a conduit connection section of the endoscopic unit.

FIG. 5 illustrates the connection section of the other end of the first suction tube 110 and the first port of the branch component 120. The outer surface of the tip of the connector component 170 that fits into the tip of the branch component 120 has a tapered surface 180 that is formed into a taper. This tapered surface is covered by the first suction tube 110 which has first been passed through a tapered ring 190 and a set screw 200. The set screw 200 is screwed onto the screw component 210 of the connector component 170 so that the first suction tube 110 is held between the tapered ring 190 and the tapered surface 180 so that this end of the first suction tube 110 is connected to the first port of the branch component 120.

The tube which pertains to the present invention may be used as a suction tube in an electronic endoscopic unit in the manner described above. In addition, it is suitable for use as a suction tube in endoscopes in which optical fibers are employed in image transmission, in endoscopes in which the insertion component is rigid or semirigid, and in other types of endoscopes other than electronic endoscopic units.

Furthermore, the tube which pertains to the present invention is also suitable for use in devices other than endoscopes, for example, as a catheter tube such as a drainage tube. In such applications, it is preferable for the tube to have a two-layer structure in which the outside of the above-mentioned tube whose pores are rubber-filled described above is covered with a second layer consisting of solidified PTFE. Other materials may be used as the second layer, as long as they are highly biocompatible. At the end of the tube, the porous structure may be solidified by subjecting it to the silicone rubber or fluorosilicone rubber filling treatment and rigidification treatment described above in order to obtain a multilayer tube whose entire surface has resistance to adhesion by organic matter.

The flexible, non-porous tube of the present invention is particularly useful as a tube for medical applications. Such medical tubes include tubes for carrying bodily fluids and forceps channel tubes. Such medical tubes must have excellent gas tightness, water tightness, high flexibility, flexing properties, and flexing resistance, as well as exceptional inner wall surface slip properties, resistance to contamination, resistance to microorganisms, and resistance to adhesion by organic matter. The tube which pertains to the present invention fulfills these conditions, and is suitable as a medical tube. The preferred diameter of the tube which pertains to the present invention, when used as a tube in medical applications, is 1 to 10 mm, and preferably 2 to 6 mm.

The flexible, non-porous tube of the present invention is particularly useful as a suction tube or conduit-forming tube in an electronic endoscopic unit.

EXAMPLES

Practical Example 1

A PTFE tube obtained by extrusion of a mixture of PTFE resin and solvent naphtha into a tube shape from an extruder was dried, the solvent naphtha contained therein removed, and the product then drawn at a temperature above 300° C. but below the melting point at a draw speed of 10% per second to yield a porous tube. This tube was then baked at a temperature at or above the melting point to yield a PTFE tube having improved gas tightness. The inside diameter of this tube was 3.2 mm, the tube wall thickness was 0.35 mm. The tube microstructure had a fibril length of 1 microns and a void content of 30%.

A solution of a silicone rubber precursor composition having the composition noted below was packed into the tube while holding it in a horizontal position, and the tube held in this fashion for 10 minutes while being slowly rotated. The solution was then drained from the tube, the composition remaining in the tube air dried, and then heated for 10 minutes at 155° C. to bring about a curing reaction of the composition to produce silicone rubber having a crosslinked structure, yielding a tube whose void spaces were filled with rubber. The tube obtained in this manner was again subjected to filling of the tube wall with crosslinked silicone rubber by the procedure described above.

Metal spheres 3.4 mm in diameter were inserted into the tube obtained in the manner described above, and the metal spheres were caused to move back and forth from end to end five times within the tube, and the inner surface of the tube was rubbed by the metal spheres so that the excess rubber coat which had formed on the inner surface was removed.

The tube obtained in this manner was essentially gas tight. Measurement of gas tightness using an Oken-type air permeability smoothness tester yielded a Gurley number of 500,000 or above. The tube did not kink (bend) even when bent to a bend radius of 10 mm, demonstrating exceptional flexibility. The inner surface of the tube was smooth and resistant to contamination. When an oil-base ink was applied to the inner surface and then wiped away with a cloth, the surface wiped clean with no traces of ink. No change in external appearance was produced during a 10,000 repetition bending test, nor was any damage produced, demonstrating exceptional flex resistance.

The silicone rubber precursor composition solution was as follows:

| | |
|---|---|
| (1) Silicone rubber precursor (KE109 (A) manufactured by Shin-Etsu Chemical Co.) | 27 weight parts |
| (2) Curing catalyst (KE109 (B) manufactured by Shin-Etsu Chemical Co.) | 3 weight parts |
| (3) Organic solvent MEK (methyl ethyl ketone) | 70 weight parts |
| (4) Solution viscosity (25° C.) | 3 cps |

Practical Example 2

A PTFE tube obtained by extrusion of a mixture of PTFE resin and solvent naphtha into a tube shape from an extruder was dried, the solvent naphtha contained therein removed, and the product then drawn at a temperature above 300° C. but below the melting point at a draw speed of 10% per second to yield a porous tube. This tube was then baked at a temperature at or above the melting point to yield a PTFE tube having improved gas tightness. The inside diameter of this tube was 3.2 mm, the tube wall thickness was 0.35 mm. The tube microstructure had a fibril length of 1 microns and a void content of 30%.

A solution of a fluorosilicone rubber precursor composition having the composition noted below was packed into the tube while holding it in a horizontal position, and the tube was held in this fashion for 10 minutes while being slowly rotated. The solution was then drained from the tube, the composition remaining in the tube air dried, and then heated for 30 minutes at 165° C. to bring about a curing reaction of the composition which produced a fluorosilicone rubber having a crosslinked structure, yielding a tube whose void spaces were filled with rubber. The tube obtained in this manner was again subjected to filling of the tube wall with crosslinked fluorosilicone rubber by the procedure described above.

Metal spheres 3.4 mm in diameter were inserted into the tube obtained in the manner described above, and the metal spheres were caused to move back and forth from end to end five times within the tube, and the inner surface of the tube was rubbed by the metal spheres so that the excess rubber coat which had formed on the inner surface was removed.

The tube obtained in this manner was essentially gas tight. Measurement of gas tightness using an Oken-type air permeability smoothness tester yielded a Gurley number of 500,000 or above. The tube did not kink (bend) even when bent to a bend radius of 10 mm, demonstrating exceptional flexibility. The inner surface of the tube was smooth and resistant to contamination. When an oil-base ink was applied to the inner surface, and then wiped away with a cloth, the surface wiped clean with no traces of ink. No change in external appearance was produced during a 10,000-repetition bending test, nor was any damage produced, demonstrating exceptional flex resistance.

The fluorosilicone rubber precursor composition solution was as follows:

| | |
|---|---|
| (1) Fluorosilicone rubber precursor (EF53 (A) manufactured by Shin-Etsu Chemical Co.) | 27 weight parts |
| (2) Curing catalyst (EF53 (B) manufactured by Shin-Etsu Chemical Co.) | 3 weight parts |
| (3) Organic solvent MEK (methyl ethyl ketone) | 70 weight parts |
| (4) Solution viscosity (25° C.) | 3 cps |

Practical Example 3

A substrate tube consisting of the porous PTFE tube filled with rubber described in Practical Example 1 was coated on its exterior surface with a solution consisting of 20 weight parts of the polymer composition indicated below in 80 weight parts ethyl methyl ketone by means of dip coating. The ethyl methyl ketone was then evaporated away under a nitrogen gas stream at 50° C., and the product was heated for two hours at 150° C. so that a vinylidene fluoride/hexafluoropropylene copolymer layer (second layer) having a crosslinked structure formed on the outside surface of the substrate tube.

The copolymer solution was as follows:

| | |
|---|---|
| (1) Vinylidene fluoride/hexafluoropropylene copolymer (Daid G-501, manufactured by Daikin Industries) | 100 weight parts |
| (2) Carbon black | 15 weight parts |
| (3) Magnesium oxide | 15 weight parts |

The second layer formed by the process described above had a thickness of approximately 50 microns, and was essentially gas tight.

Next, the outer surface of the second layer formed in the manner described above was covered with a porous PTFE film (thickness 100 microns; width 24 mm) having a pore diameter of 1 micron and a void content of 30%, which was wound around twice in spiral fashion to form a third layer (thickness 200 microns). The entire assembly was then heated for 1.5 minutes at approximately 380° C., the copolymer of the second layer softened, and the layers fused into a single unit.

The inner surface of the three-layer tube obtained in this manner was impregnated with the silicone rubber precursor composition of Practical Example 1 by the same procedure used in Practical Example 1. The solvent was then removed and the product heat-cured to yield a a tube whose tube wall void spaces were filled with silicone rubber having a crosslinked structure. The silicone rubber filling operation was then repeated. Finally, the silicone rubber coat adhering to the tube wall surface was removed using the procedure described in Practical Example 1.

The three-layer tube obtained in this manner was essentially gas tight. Measurement of gas tightness using an Oken-type air permeability smoothness tester yielded a Gurley number of 500,000 or above. The tube did not kink (bend) even when bent to a bend radius of 10 mm, demonstrating exceptional flexibility. The inner surface of the tube was smooth and resistant to contamination. When an oil-base ink was applied to the inner surface, and then wiped away with a cloth, the surface wiped clean with no traces of ink. No change in external appearance was produced during a 10,000-repetition bending test, nor was any damage produced, demonstrating exceptional flex resistance.

Practical Example 4

A three layer tube was obtained by the procedure of Practical Example 3, with the exception that the fluorosilicone rubber precursor composition of Practical Example 2 was used in place of the silicone rubber precursor composition. Like the tube obtained in Practical Example 3, this tube was essentially gas tight, and its inner surface had exceptional slip properties, flexing properties, resistance to contamination, and flexing resistance.

We claim:

1. A flexible tube comprising a tubular substrate of porous expanded polytetrafluoroethylene having a microstructure of nodes interconnected by fibrils and having void spaces between fibrils, said tube having an outer surface and a luminal surface, wherein the void spaces adjacent to the luminal surface are filled with silicone rubber such that the luminal surface comprises a non-porous surface of polytetrafluoroethylene and silicone rubber wherein a continuous coat of said silicone rubber is not present on the luminal surface of said tube, and wherein the void spaces adjacent to the outer surface are open.

2. A flexible tube according to claim 1 wherein the silicon rubber is a fluorosilicone rubber.

3. A flexible tube according to claim 1 comprising an endoscope channel tube.

4. A flexible tube according to claim 2 comprising an endoscope channel tube.

5. A flexible tube comprised of porous polytetrafluoroethylene having a microstructure of nodes interconnected by fibrils and having void spaces between fibrils, said tube having a luminal surface and having a wall thickness comprising a first portion and a second portion wherein said second portion concentrically surrounds said first portion and said first portion includes said luminal surface, wherein the void spaces of said second portion are open and wherein the void spaces of said first portion are filled with silicone rubber, and wherein the luminal surface comprises polytetrafluoroethylene and silicone rubber wherein a continuous coat of said silicone rubber is not present on the luminal surface of said tube.

6. A flexible tube according to claim 5 wherein the silicone rubber is fluorosilicone rubber.

7. A flexible tube according to claim 5 comprising an endoscope channel tube.

8. A flexible tube according to claim 6 comprising an endoscope channel tube.

* * * * *